(12) United States Patent
Konstandopoulos et al.

(10) Patent No.: US 8,056,405 B2
(45) Date of Patent: Nov. 15, 2011

(54) PARTICULATE MATTER CONCENTRATION MEASURING APPARATUS

(75) Inventors: Athanasios G. Konstandopoulos, Salonika (GR); Fumishige Miyata, Gifu (JP); Takafumi Kasuga, Gifu (JP); Yasuhiro Ishii, Gifu (JP)

(73) Assignees: Ibiden Co., Ltd., Ogaki-Shi (JP); Athanasios G. Konstandopoulos, Thessaloniki (GR)

( * ) Notice: Subject to any disclaimer, the term of this patent is extended or adjusted under 35 U.S.C. 154(b) by 129 days.

(21) Appl. No.: 12/694,289

(22) Filed: Jan. 27, 2010

(65) Prior Publication Data
US 2010/0242456 A1 Sep. 30, 2010

(30) Foreign Application Priority Data

Mar. 31, 2009 (JP) .................... PCT/JP2009/056750

(51) Int. Cl.
*G01M 15/10* (2006.01)
(52) U.S. Cl. .................................................. 73/114.71
(58) Field of Classification Search ............... 73/114.71, 73/114.75, 114.76
See application file for complete search history.

(56) References Cited

U.S. PATENT DOCUMENTS

| | | | |
|---|---|---|---|
| 6,517,786 B1 | 2/2003 | Best et al. | |
| 7,472,610 B2* | 1/2009 | Clerc et al. | 73/862.52 |
| 7,658,064 B2* | 2/2010 | Konstandopoulos | 60/297 |
| 7,866,146 B2* | 1/2011 | Konstandopoulos | 60/311 |
| 7,891,176 B2* | 2/2011 | Konstandopoulos | 60/297 |
| 2008/0087007 A1* | 4/2008 | Konstandopoulos | 60/286 |
| 2008/0087101 A1 | 4/2008 | Konstandopoulos | |
| 2008/0134796 A1* | 6/2008 | Clerc et al. | 73/756 |
| 2010/0242455 A1* | 9/2010 | Konstandopoulos et al. | 60/311 |
| 2010/0242457 A1* | 9/2010 | Konstandopoulos et al. | 60/311 |
| 2010/0242463 A1* | 9/2010 | Konstandopoulos et al. | 60/324 |
| 2011/0061368 A1* | 3/2011 | Miyata et al. | 60/277 |
| 2011/0072789 A1* | 3/2011 | Konstandopoulos et al. | 60/276 |

FOREIGN PATENT DOCUMENTS

| | | |
|---|---|---|
| EP | 1916394 | 4/2008 |
| JP | 2001-522302 | 11/2001 |
| JP | 2002-285822 | 10/2002 |
| JP | 2006-231111 | 9/2006 |
| JP | 2008-101605 | 5/2008 |
| JP | 2008-212787 | 9/2008 |

\* cited by examiner

*Primary Examiner* — Freddie Kirkland, III
(74) *Attorney, Agent, or Firm* — Ditthavong Mori & Steiner, P.C.

(57) ABSTRACT

A particulate matter concentration measuring apparatus configured to measure concentration of particulate matter in exhaust gas passing through an exhaust line includes an exhaust gas collecting line branched from the exhaust line, a particulate matter detection filter provided in the exhaust gas collecting line, a differential pressure sensor configured to sense differential pressure between an inlet and an outlet of the particulate matter detection filter, a passage wall disposed so that the exhaust gas flows to a downstream side of the particulate matter detection filter, an inlet side passage through which the exhaust gas flows into the particulate matter detection filter in the passage wall, and an outlet side passage through which the exhaust gas flows out from the particulate matter detection filter. The outlet side passage has an outlet side cross-sectional area approximately 1.0 times or more larger than an inlet side cross-sectional area of the inlet side passage.

8 Claims, 16 Drawing Sheets

PARTICULATE MATTER CONCENTRATION MEASURING APPARATUS

CROSS-REFERENCE TO RELATED APPLICATIONS

The present application is a continuation of PCT/JP2009/056750, filed Mar. 31, 2009. The contents of this application are incorporated herein by reference in their entirety.

BACKGROUND OF THE INVENTION

1. Field of the Invention

The present invention relates to a particulate matter concentration measuring apparatus configured to measure the concentration of particulate matter (PM) included in exhaust gas.

2. Discussion of the Background

FIG. 1 shows a known particulate matter concentration measuring apparatus 20PM (PM sensor), as described in EP1916394A1, capable of detecting the concentration of particulate matter (PM) including carbon (C) as a main component in exhaust gas of a diesel engine. As shown in FIG. 1, the particulate matter concentration measuring apparatus 20PM includes an exhaust line 21, a secondary exhaust line 21A branching from the exhaust line 21, a particulate matter detection filter 22A provided in the secondary exhaust line 21A, and a differential pressure sensor 22B measuring differential pressure between inlet and outlet of the particulate matter detection filter 22A. Further, in the secondary exhaust line 21A, a flow rate meter 24 and a temperature sensor T1 are provided. Further, in the particulate matter detection filter 22A, a heater 22H is provided.

According to Patent EP1916394A1, in the particulate matter concentration measuring apparatus 20PM, a differential pressure ΔP across the particulate matter detection filter 22A, a temperature T of exhaust gas in the secondary exhaust line 21A, and a flow amount Q2 of exhaust gas in the secondary exhaust line 21A are measured. Then, based on the measured values of the differential pressure ΔP, the temperature T of the exhaust gas, and the flow amount Q2 of the exhaust gas, a value of PM [g/h] which is the mass of particulate matter (PM) collected on the particulate matter detection filter 22A per unit time is calculated. Based on the PM [g/h] which is the mass of particulate matter (PM), a value of PMconc [g/cm$^3$] which is the concentration of particulate matter (PM) in the exhaust gas is calculated. In this case, if a large amount of particulate matter (PM) is accumulated on the particulate matter detection filter 22A, detection accuracy of the differential pressure ΔP may be more likely to be degraded. To overcome the problem, in the particulate matter concentration measurement according to EP1916394A1, a heater 22H is provided so as to burn and remove particulate matter (PM) when the particulate matter (PM) is accumulated on the particulate matter detection filter 22A to some extent.

Further, EP1916394A1 discloses a Diesel Particulate Filter (DPF) 22 made of porous ceramic material and provided in the exhaust line 21 of an exhaust gas purification apparatus 20. Further, the secondary exhaust line 21A is connected to the exhaust line 21 on the upstream side of the Diesel Particulate Filter (DPF) 22, and based on a value of PMconc [g/m$^3$] which is concentration of particulate matter (PM) in exhaust gas and an engine operating status or a flow amount Q1 of the exhaust gas introduced into the Diesel Particulate Filter (DPF) 22, a value of PMenter-full-filter [g/h] which is the mass of particulate matter (PM) introduced into the Diesel Particulate Filter (DPF) 22 is calculated.

Similar to the particulate matter detection filter 22A, in the Diesel Particulate Filter (DPF) 22, the collected particulate matter (PM) is likely to be gradually accumulated with continuous use of the Diesel Particulate Filter (DPF) 22. If the accumulation of the particulate matter (PM) in the Diesel Particulate Filter (DPF) 22 is ignored, a pressure caused by exhaust gas may become too high, which may lower fuel economy and/or cause engine damage.

To avoid the problems, in the exhaust gas purification apparatus 20 using the Diesel Particulate Filter (DPF) 22, the accumulated particulate matter (PM) is burned and removed at regular intervals in the Diesel Particulate Filter (DPF) 22 so as to regenerate the Diesel Particulate Filter (DPF) 22.

To regenerate the Diesel Particulate Filter (DPF) 22, high-temperature exhaust gas is introduced into the Diesel Particulate Filter (DPF) 22 so that the accumulated particulate matter (PM) can be burned and removed.

EP1916394A1 describes that, by obtaining the value of PMenter-full-filter [g/h] which is the mass of particulate matter (PM) collected on the Diesel Particulate Filter (DPF) 22, it becomes possible to accurately determine whether an amount of particulate matter (PM) having been actually collected on the Diesel Particulate Filter (DPF) 22 exceeds a predetermined threshold value which necessitates the regeneration of the Diesel Particulate Filter (DPF) 22.

SUMMARY OF THE INVENTION

According to an aspect of the present invention, a particulate matter concentration measuring apparatus configured to measure concentration of particulate matter in exhaust gas passing through an exhaust line of a diesel engine includes an exhaust gas collecting line, a particulate matter detection filter, a differential pressure sensor, a passage wall, an inlet side passage, and an outlet side passage. The exhaust gas collecting line is branched from the exhaust line and has a cross-sectional area smaller than a cross-sectional area of the exhaust line. The particulate matter detection filter is provided in the exhaust gas collecting line. The differential pressure sensor is configured to sense differential pressure between an inlet and an outlet of the particulate matter detection filter. The passage wall is disposed so that the exhaust gas flows to a downstream side of the particulate matter detection filter. The exhaust gas flows into the particulate matter detection filter in the passage wall through the inlet side passage. The exhaust gas flows out from the particulate matter detection filter through an outlet side passage. The outlet side passage defines a space having an outlet side cross-sectional area approximately 1.0 times or more larger than an inlet side cross-sectional area of a space defined by the inlet side passage. The outlet side cross-sectional area and the inlet side cross-sectional area are substantially perpendicular to a longitudinal axis of the particulate matter detection filter.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

Figure 1:
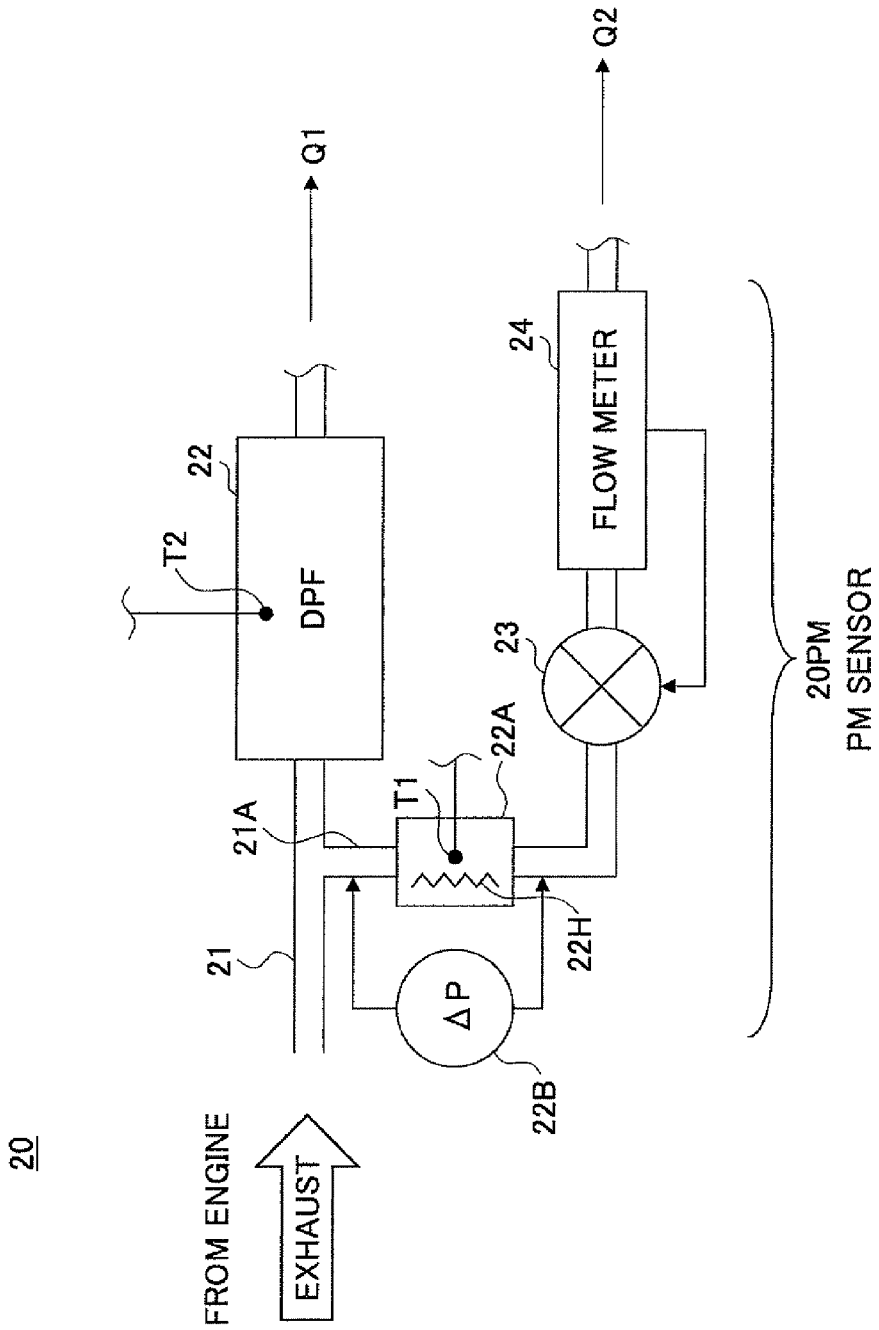
FIG. 1 is a schematic drawing showing a configuration of a conventional exhaust gas purification apparatus.

The embodiments will now be described with reference to the accompanying drawings, wherein like reference numerals designate corresponding or identical elements throughout the various drawings.

First Embodiment

Figure 2:
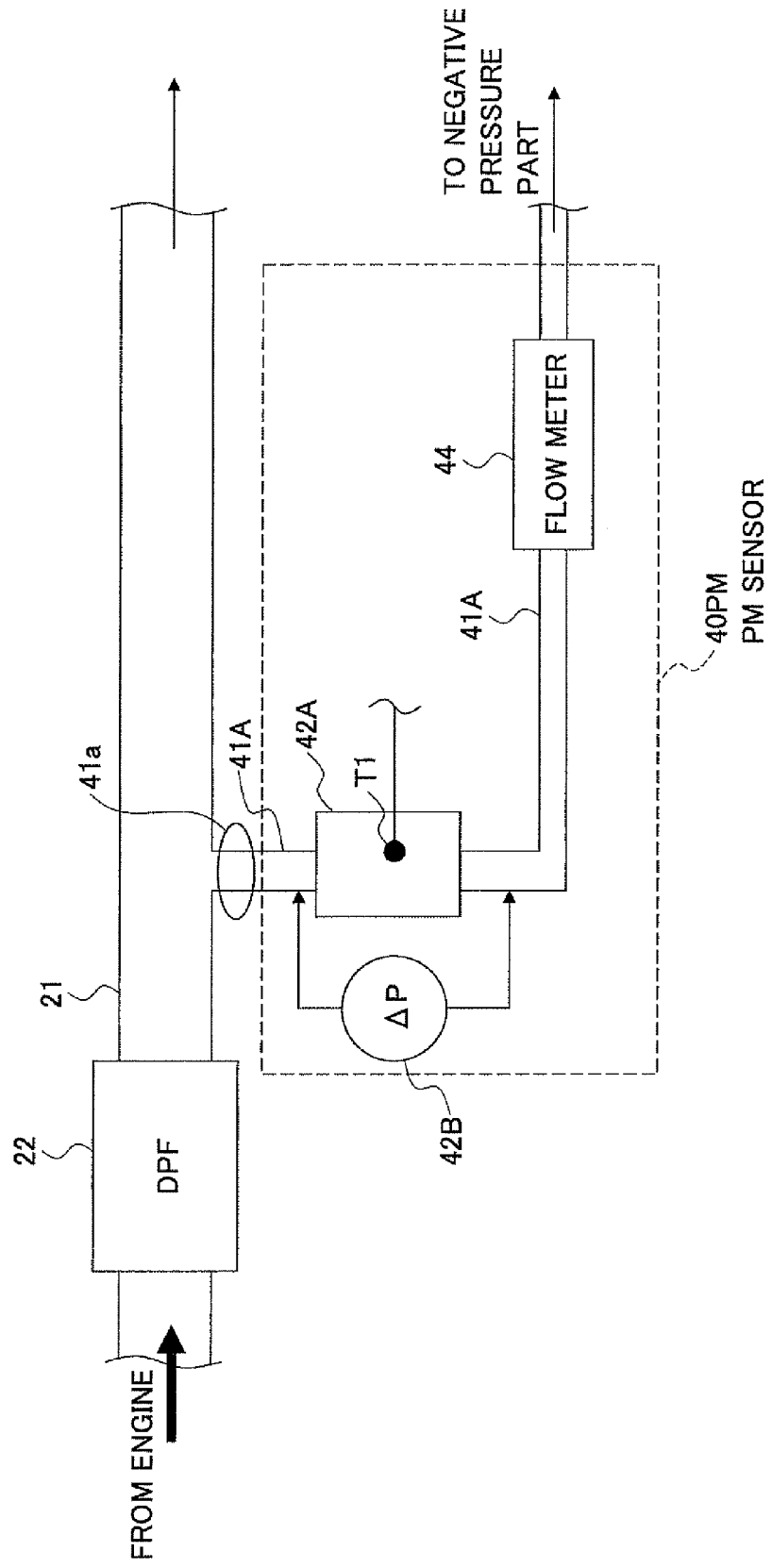
FIG. 2 is a drawing showing an exemplary configuration of an exhaust gas purification apparatus using a particulate matter concentration measuring apparatus according to a first embodiment of the present invention.

FIG. 2 shows an exemplary configuration of a particulate matter concentration measuring apparatus 40PM according to a first embodiment of the present invention. In FIG. 2, the same reference numerals are used for the same or equivalent elements described above and the descriptions thereof may be omitted. In the particulate matter concentration measuring apparatus 40PM (PM sensor) of FIG. 2, in a case where a problem occurs in the Diesel Particulate Filter (DPF) 22 and a larger amount of particulate matter (PM) than a predetermined threshold value leaks into the downstream side of the Diesel Particulate Filter (DPF) 22 in the exhaust line 21, the problem (leakage) can be detected so as to flash or turn on an alarm or a lamp and the like.

As shown in FIG. 2, according to the first embodiment of the present invention, there is provided an exhaust gas collecting line 41A having an exhaust gas collection section 41a on one end thereof and there is also provided the Diesel Particulate Filter (DPF) 22 in the exhaust line 21 from a diesel engine, so that the exhaust gas collecting line 41A is connected to the exhaust line 21 on the downstream side of the Diesel Particulate Filter (DPF) 22. Further, in the exhaust gas collecting line 41A, a particulate matter detection filter 42A illustrated in detail in FIG. 3 and a flow meter 44 are connected in series. Further, the exhaust gas collecting line 41A is connected to a negative-pressure tank, an air intake section or the like where pressure is lower than that at the inlet of the particulate matter detection filter 42A, so that exhaust gas in the exhaust line 21 is drawn into the particulate matter detection filter 42A. This provides the same effect as that obtained by connecting a suction pump on the downstream side of the exhaust gas collecting line 41A, which makes it possible to reliably supply exhaust gas to the particulate matter detection filter 42A.

Further, in the particulate matter detection filter 42A, there are provided a temperature sensor T1 for measuring temperature of the particulate matter detection filter 42A and a differential pressure sensor 42B for measuring differential pressure across the particulate matter detection filter 42A. The size of a flow passage cross-sectional area of the exhaust gas collection section 41a is smaller than that of the exhaust line 21.

As the differential pressure sensor 42B, a known manometer (pressure gauge) such as a diaphragm gauge, a strain-gauge-type, Bellows-type, or thermal-type manometer may be used. Further, as the flow meter 44, a known flow meter such as a hot wire flow meter, a venturi flow meter may be used.

Figure 3:
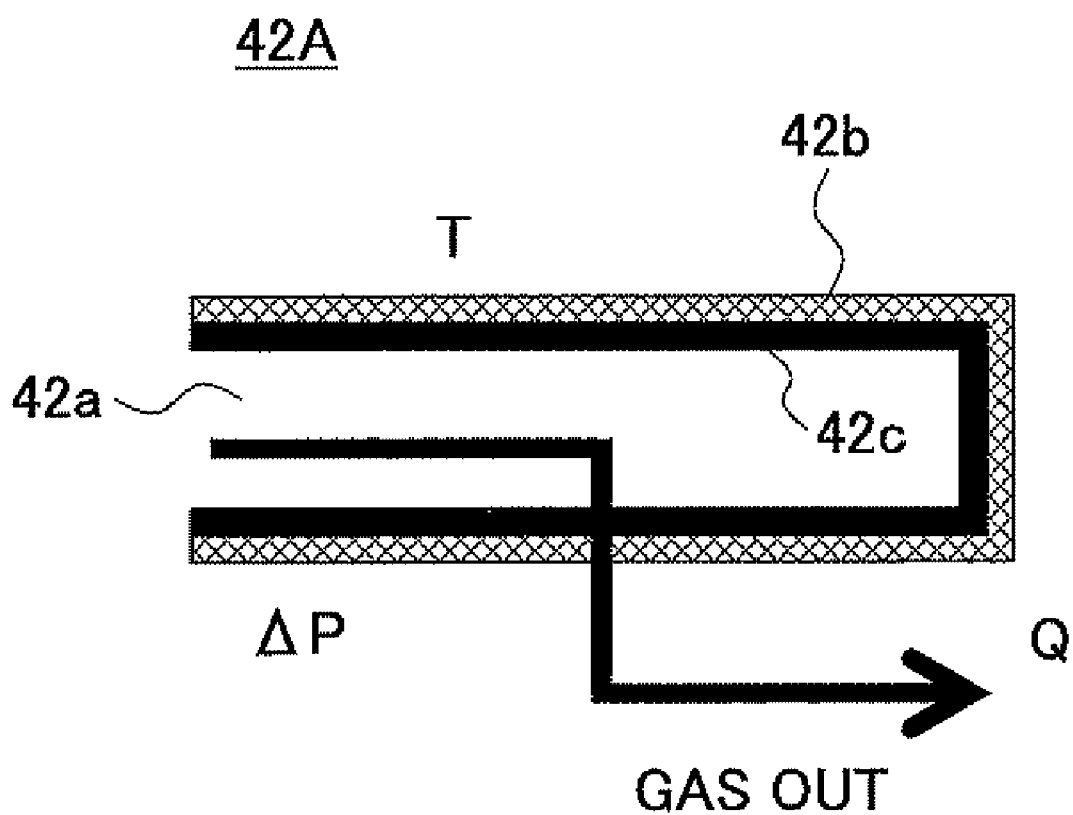
FIG. 3 is a drawing showing an operation of a particulate matter detection filter in the particulate matter concentration measuring apparatus according to the first embodiment of the present invention.

FIG. 3 shows an exemplary configuration of the particulate matter detection filter 42A according to the first embodiment of the present invention. In the configuration of FIG. 3, the particulate matter detection filter 42A has a single cell 42b only. However, for example, the particulate matter detection filter 42A may be formed by stacking plural cells 42b as shown in FIG. 17.

According to this embodiment of the present invention, a total volume of one or plural gas passages 42a of the particulate matter detection filter 42A is set to be equal to or less than approximately 5% (e.g., in a range from approximately 0.05% to approximately 5%) of the total volume of the exhaust gas passage in the Diesel Particulate Filter (DPF) 22 or equal to or less than approximately 65 ml (e.g., in a range from approximately 0.05 ml to approximately 65 ml) or the filtration area of one or plural gas passages 42a (see FIG. 3) of the particulate matter detection filter 42A is set in a range from approximately 0.1 $cm^2$ to approximately 1,000 $cm^2$ (preferably in a range from approximately 1 $cm^2$ to approximately 10 $cm^2$). Further, the gas passage 42a is formed so as to have a rectangular cross-sectional shape or the like and one end thereof being closed (the rear (right-hand) side of the gas passage 42a is closed as shown in FIG. 3).

Figure 17:
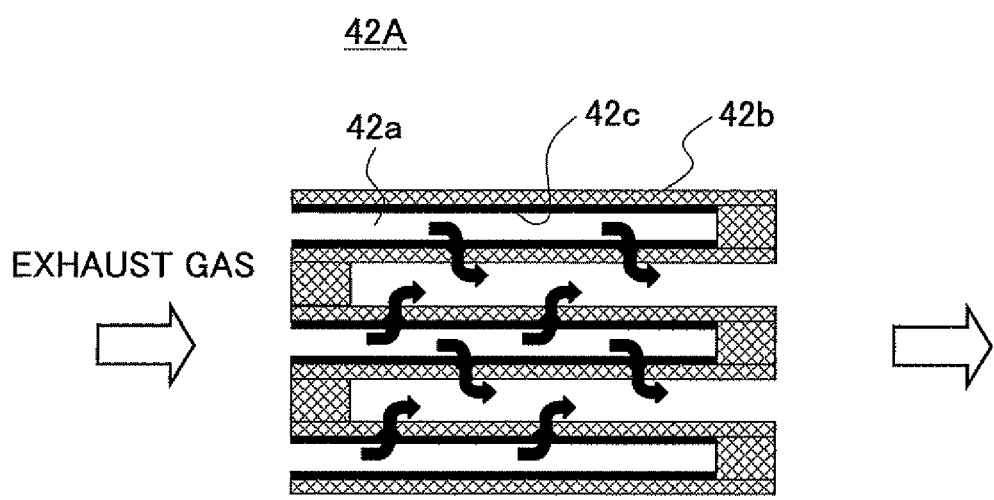
FIG. 17 is a drawing showing a modification of the particulate matter detection filter according to the first embodiment of the present invention.

In FIGS. 3 and 17, according to the first embodiment of the present invention, each cell 42b formed of porous ceramic material has an inflow-side gas passage 42a formed by closing one end of the cell 42b and leaving the other end open, so that exhaust gas introduced into the inflow-side gas passage 42a passes through the cell wall made of porous ceramic material to flow into an adjoining inflow-side gas passage 42a. During the flow, particulate matter (PM) is trapped (collected) on an inner wall surface of the cell 42b, so that a particulate matter layer 42c is formed on the inner wall surface of the cell 42b.

Figure 4:
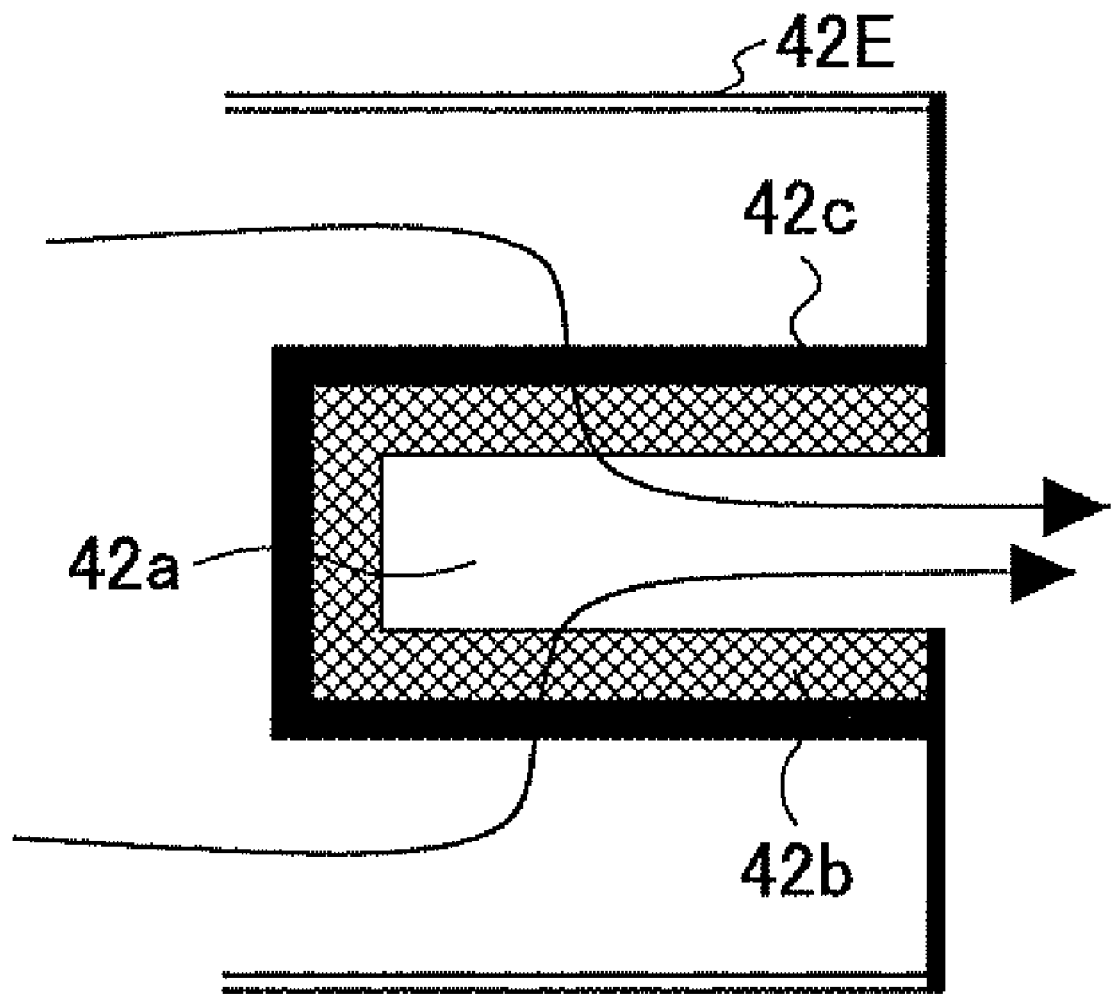
FIG. 4 is a drawing showing a modification of the particulate matter detection filter in the particulate matter concentration measuring apparatus according to the first embodiment of the present invention.

FIG. 4 shows a modification (modified example) of the cell 42b in FIG. 3 of the first embodiment of the present invention. Unlike the case of FIG. 3, in the case of FIG. 4 of the first embodiment of the present invention, exhaust gas passes through the cell wall of the cell 42b from the inflow-side gas passage which is outside of the cell 42b and flows into the outflow-side gas passage 42a (see FIG. 4) formed inside the cell 42b, so that the deposition of the particulate matter layer 42c is formed on the outer wall surface of the cell 42b. In FIG. 17, the particulate matter detection filter 42A is formed by, for example, alternately adjoining (laminating) the cell 42b in FIG. 3 and the cell 42b in FIG. 4.

The cells having a similar configuration shown in FIG. 17 may be formed in the Diesel Particulate Filter (DPF) 22 described with reference to FIG. 1. However, it is not always necessary that the size and/or the cross-sectional shape of gas passage of the particulate matter detection filter 42A are substantially the same as those of the Diesel Particulate Filter (DPF) 22. For example, the cross-sectional shape of gas passage of the particulate matter detection filter 42A may be any sectional shape such as a substantially circular shape, substantially square shape, substantially octagon shape, substantially elliptic shape. Further, it is not always necessary that the porous ceramic material of the cell of the particulate matter detection filter 42A is substantially the same as that of the Diesel Particulate Filter (DPF) 22. For example, the material of the cell of the particulate matter detection filter 42A may be material other than ceramic. As described above, by configuring that the total volume of one or plural gas passages 42a of the particulate matter detection filter 42A is set to be equal to or less than approximately 5% (e.g., in a range from approximately 0.05% to approximately 5%) of the total volume of the exhaust gas passage in the Diesel Particulate Filter (DPF) 22 or equal to or less than approximately 65 ml (e.g., in a range from approximately 0.05 ml to approximately 65 ml) or the filtration area of one or plural gas passage 42a of the particulate matter detection filter 42A is set in a range from approximately 0.1 cm$^2$ to approximately 1,000 cm$^2$ (preferably in a range from approximately 1 cm$^2$ to approximately 10 cm$^2$), it may become possible to provide a uniform deposition of the particulate matter layer 42c on the surface of the cell 42b; thereby enabling simple and accurate measurement of accumulation amount of particulate matter (PM) in the Diesel Particulate Filter (DPF) 22.

In the particulate matter concentration measuring apparatus 40PM of FIG. 2 according to the first embodiment of the present invention, a soot load amount of the particulate matter (PM) collected on the particulate matter detection filter 42A is calculated based on the following formula:

$$\Delta P = \frac{\mu Q}{2 V trap} (\alpha + W s)^2 \left[ \begin{array}{c} \frac{W s}{K w \alpha} + \frac{1}{2 K s o o t} \ln\left(\frac{\alpha}{\alpha - 2 W}\right) + \\ \frac{4 F L^2}{3} \left( \frac{1}{(\alpha - 2 W)^4} + \frac{1}{\alpha^4} \right) \end{array} \right] + \frac{\rho Q^2 (\alpha + W s)^4}{V trap^2} \left[ \frac{\beta W s}{4} + 2 \zeta \left[ \frac{L}{\alpha} \right]^2 \right] \qquad \text{formula (1)}$$

where the symbol "$\Delta P$" denotes the differential pressure expressed in [Pa]; the symbol "$\mu$" denotes the kinetic viscosity coefficient expressed in [Pa·s]; the symbol "Q" denotes the flow rate of exhaust gas expressed in [m$^3$/h]; the symbol "$\alpha$" denotes the length of a side of the cell expressed in [m]; the symbol "$\rho$" denotes the density of exhaust gas expressed in [g/m$^3$]; the symbol) "Vtrap" denotes the filter volume expressed in [m$^3$]; the symbol "Ws" denotes the wall thickness expressed in [m]; the symbol "Kw" denotes the gas permeability of the wall expressed in [m$^{-1}$]; the symbol "Ksoot" denotes the gas permeability of the collected particulate matter layer expressed in [m$^{-1}$]; the symbol "W" denotes the thickness of the collected particulate matter layer expressed in [m]; the symbol "F" denotes the numerical coefficient (=28.454); the symbol "L" denotes the effective filter length expressed in [m]; the symbol "$\beta$" denotes the Forchheimer coefficient of the porous wall expressed in [m$^{-1}$]; and the symbol "$\zeta$" denotes the differential pressure due to pass through the filter expressed in [Pa].

Next, a value of "msoot" which is the mass of the particulate matter (PM) collected on the particulate matter detection filter 22A (cell 42b) is calculated based on the following formula:

$$W = \frac{\alpha - \sqrt{\alpha^2 - \frac{msoot}{Ncells \times L \times \rho soot}}}{2} \qquad \text{formula (2)}$$

where the symbol "msoot" denotes the mass of the collected particulate matter (PM) expressed in [g]; the symbol "Ncells" denotes an aperture number of the cell at the inlet side; and the symbol "$\rho$soot" denotes the density of the collected particulate matter (PM).

Then, a value of "PM [g/s]" which is a collection amount per unit time is obtained by dividing "msoot" by the elapsed time [s] since the previous regeneration of the particulate matter detection filter 22A.

After obtaining "PM [g/s]" which is same as the mass of deposited particulate matter (PM) per unit time, it becomes possible to obtain a value of "PMconc [g/m$^3$]" which is the concentration of the particulate matter (PM) in exhaust gas based on the obtained "PM [g/s]" and a value of "Q2 [m$^3$/s]" which is the flow rate of exhaust gas passing through the particulate matter detection filter 22A according to the following formula.

$$PM\ [g/s] = Mconc\ [g/m^3] \times Q2\ [m^3/s] \qquad \text{formula (3)}$$

As shown in FIG. 2, according to the first embodiment of the present invention, by providing the particulate matter concentration measuring apparatus 40PM on the downstream side of the Diesel Particulate Filter (DPF) 22, in a case where a problem occurs in the Diesel Particulate Filter (DPF) 22 and a larger amount of particulate matter (PM) than a predetermined threshold value leaks into the downstream side of the Diesel Particulate Filter (DPF) 22 in the exhaust line 21, the problem may be immediately detected, which may enable to flash or turn on an alarm or a lamp and the like.

In such a particulate matter concentration measuring apparatus 40PM, it may become possible to further improve the accuracy of the measurement.

Figure 5:
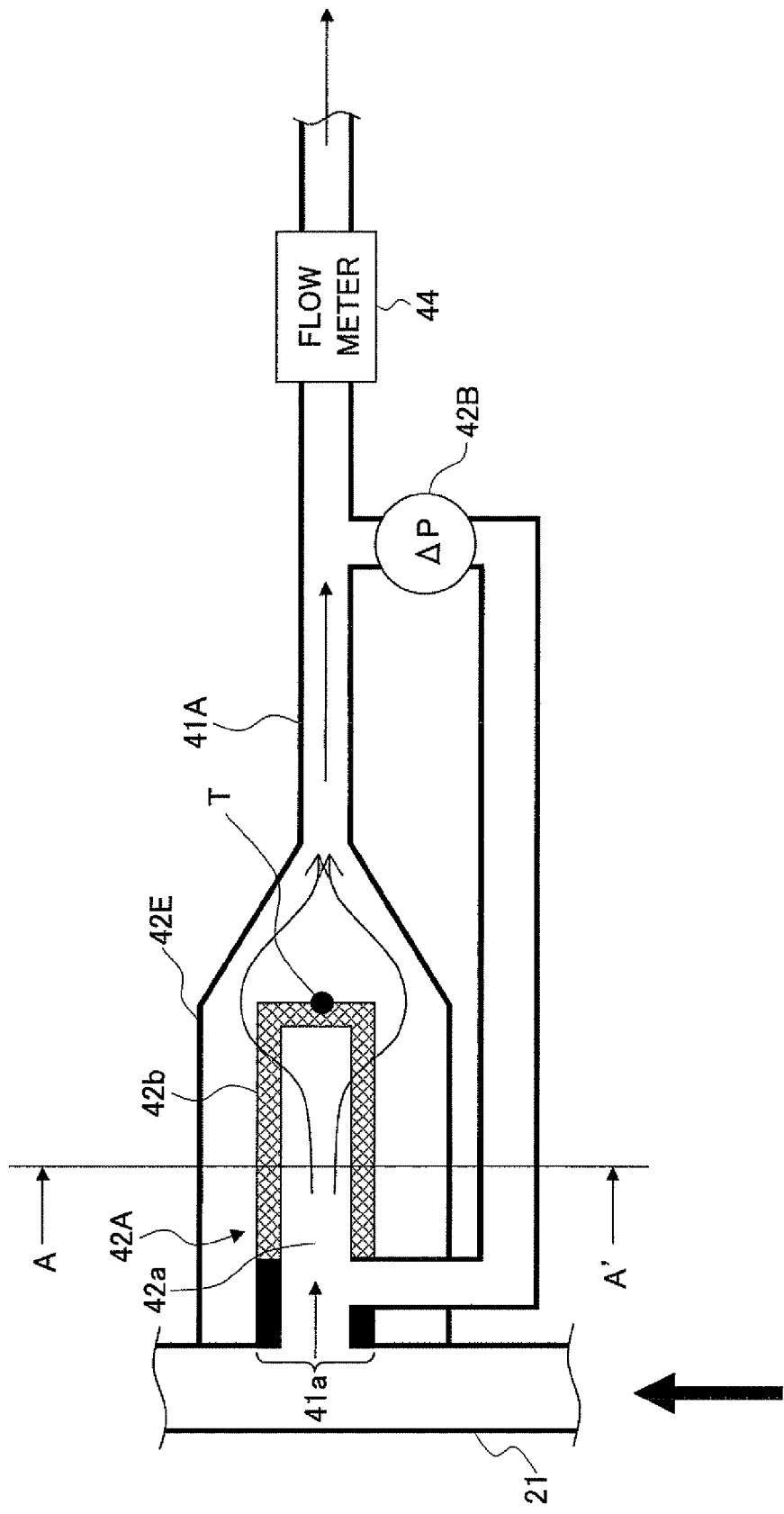
FIG. 5 is a drawing showing an exemplary more detailed configuration the particulate matter concentration measuring apparatus according to the first embodiment of the present invention.

FIG. 5 shows a more detailed exemplary configuration of the particulate matter concentration measuring apparatus 40PM according to the first embodiment of the present invention shown in FIG. 2.

As shown in FIG. 5, according to the first embodiment of the present invention, the particulate matter detection filter 42A includes the exhaust gas collection section 41a formed on one end of the particulate matter detection filter 42A and is housed inside a housing 42E defining the exhaust gas collecting line 41A. The differential pressure sensor 42B, which may be a diaphragm gauge, is provided on the downstream side of the particulate matter detection filter 42A. One end of the differential pressure sensor 42B is connected to the upstream side of the particulate matter detection filter 42A, and the other side of the differential pressure sensor 42B is connected to the exhaust gas collecting line 41A on the downstream side of the particulate matter detection filter 42A. As a result of this configuration, it may become possible for the differential pressure sensor 42B to measure the differential pressure across the cell 42b of the particulate matter detection filter 42A.

Figure 6:
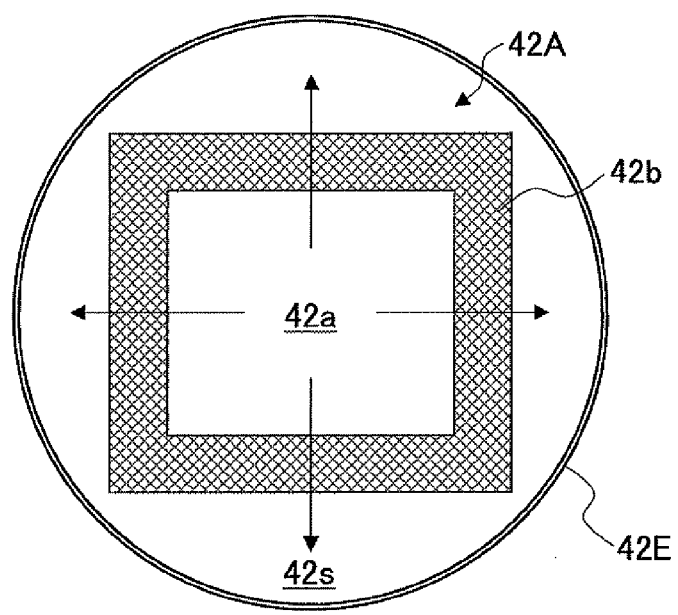
FIG. 6 is a partial cross-sectional drawing along the line A-A' in FIG. 5.

FIG. 6 shows a partial cross-sectional view of the particulate matter concentration measuring apparatus 40PM with the housing 42E along A-A' line in FIG. 5.

As FIG. 6 illustrates, according to the first embodiment of the present invention, exhaust gas introduced into the gas passage 42a passes through the cell 42b of the particulate matter detection filter 42A, flows into a space 42s defined between the particulate matter detection filter 42A and the housing 42E, and further flows to the downstream side of the exhaust gas collecting line 41A.

Figure 7A:
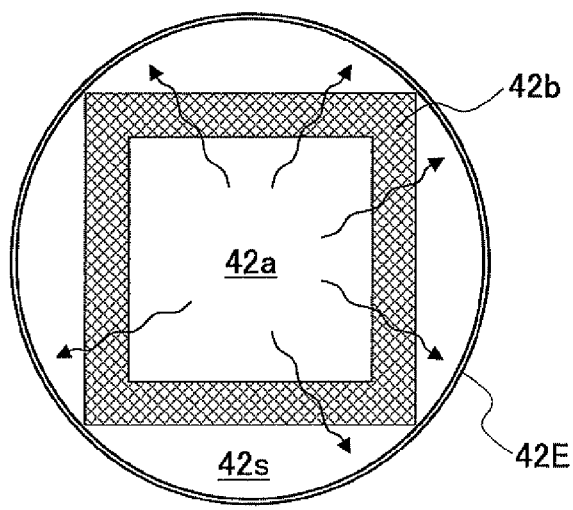
FIGS. 7A and 7B are explanatory drawings illustrating a problem to be solved in the first embodiment of the present invention.
Figure 7B:
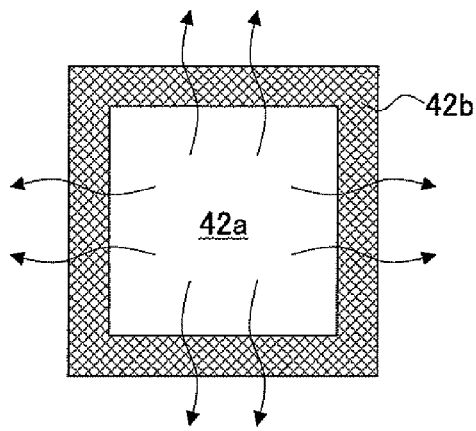

In the particulate matter concentration measuring apparatus 40PM having the configuration described above, when the outer diameter (outer circumference) of the housing 42E is decreased, the inner diameter (inner circumference) of the housing 42E may be accordingly decreased. In this case, as shown in FIG. 7A, the outer space of the cell 42b between the outer surface of the cell 42b and the inner surface of housing 42E, i.e., the space 42s between the outer surface of the cell 42b and the passage wall facing the cell 42b and defining the passage of exhaust gas, may become narrower. In such a case, compared with a case where the cell 42b is disposed in a free space as shown in FIG. 7B, the size of the total cross-sectional area of the outer space 42s is decreased; therefore, a value detected by the differential pressure sensor 42B may be more influenced by a factor other than soot deposited in the particulate matter detection filter 42A. As a result, the value of "PMconc [g/m$^3$]" (i.e., the concentration of the particulate matter (PM) in exhaust gas) calculated based on the formulas (1) through (3) may have some measurement error.

Figure 8:
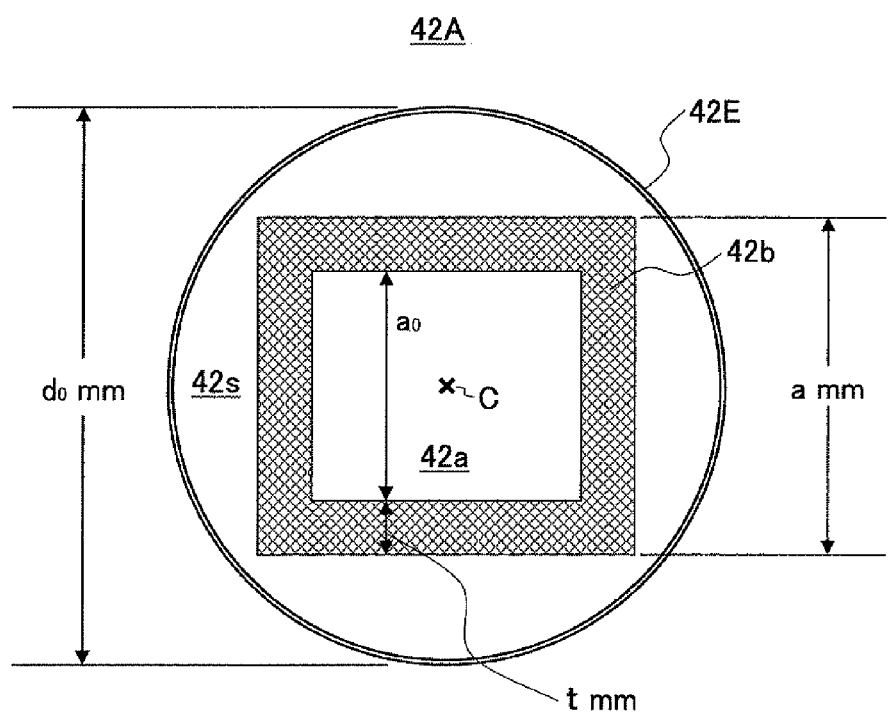
FIG. 8 is a drawing showing definitions of parameters used in the particulate matter concentration measuring apparatus according to the first embodiment of the present invention.

The behavior of the measurement error has been studied by comparing the values of the concentration of the particulate matter (PM) in exhaust gas based on the above formulas (1) through (3) with the corresponding true values by changing the values of the parameters which are the internal diameter "$d_o$" of the housing 42E, the length of a side "$a_o$" in the rectangular cross-section at the inlet side of the cell 42b, and the wall thickness "t" of the cell 42b as shown in FIG. 8.

More specifically, in the research, the measurement error is obtained by assuming that the measured value of the particulate matter (PM) in the exhaust line 21 of the configuration of FIG. 2 of the first embodiment of the present invention (described below) is regarded as the true value and by comparing the difference between the true value and the value of the concentration of the particulate matter (PM) in exhaust gas based on the above formulas (1) through (3).

Figure 9:
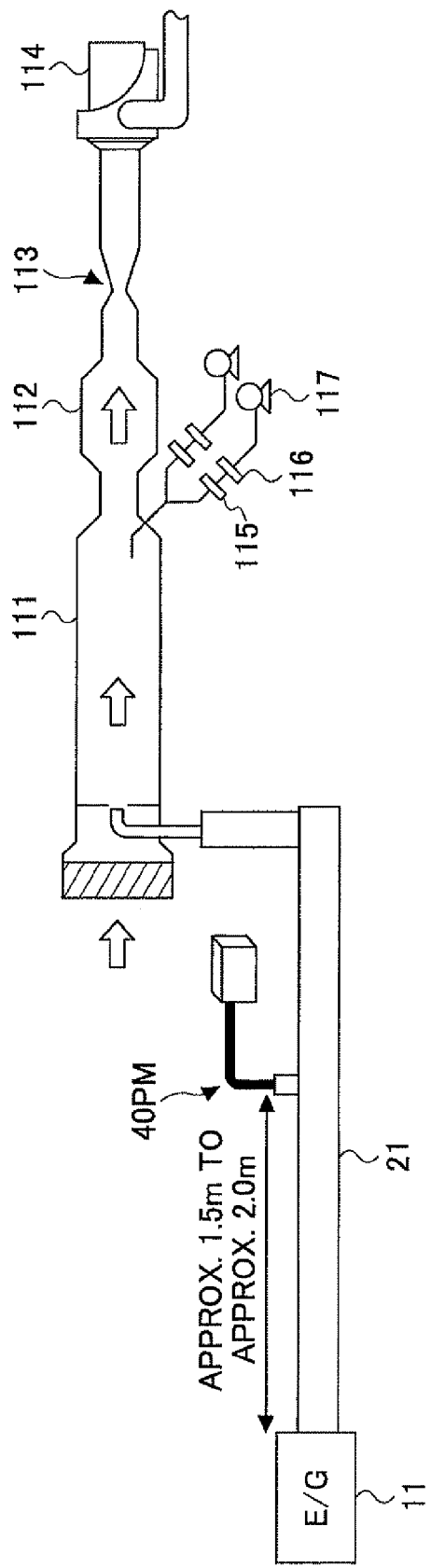
FIG. 9 is a drawing showing an experiment to obtain a true value of the concentration of the particulate matter according to the first embodiment of the present invention.

As shown in FIG. 9, according to the first embodiment of the present invention, exhaust gas exhausted from a diesel engine 11 into the exhaust line 21 is introduced into a dilution tunnel 111 to which clean air also is being introduced to dilute and cool the exhaust gas to a temperature equal to or less than 52° C. Then the cooled exhaust gas is collected on a primary collection filer 115 and a secondary collection filter 116, so that the mass of the filters with collected particulate matter (PM) is measured using a microbalance to directly measure the amount of particulate matter (PM) in the exhaust gas. Then, the measured amount of the particulate matter (PM) is converted into the value of the concentration of the exhaust gas in the exhaust line 21 and the obtained value is defined as the true value. The measurement error is obtained by comparing the true value with the calculated value of "PMconc [g/m$^3$]" of the particulate matter concentration measuring apparatus 40PM (distance between diesel engine (E/G) 11 and particulate matter concentration measuring apparatus 40PM is approximately 1.5 m to approximately 2.0 m) provided in the same exhaust line 21. In the configuration according to the first embodiment of the present invention shown in FIG. 9, after passing through the dilution tunnel 111, exhaust gas further passes through a heat exchanger 112 and a critical flow venturi tube 113 and is suctioned by a blower 114. Other blowers 117 are also provided on the downstream side of the primary collection filer 115 and the secondary collection filter 116 to suction the exhaust gas.

Table 1, described below, shows the measurement errors between the calculation values and true values of the concentration of particulate matter (PNM) obtained as described above in examples 1 through 7 and comparative examples 1 through 3 which vary depending on the values of the parameters described above. Further, in Table 1, the term "Area ratio" refers to a ratio defined as "A1/A2", where the symbol "A1" denotes the cross-sectional area of the outer space 42s (i.e., the outflow-side gas passage of the cell 42b) and the symbol "A2" denotes the cross-sectional area of the inflow-side gas passage of the cell 42 (=$a_o^2$). Further, in Table 1, comparative examples differ from examples in that the measurement error exceeds 10%.

TABLE 1

| | t [mm] | d0 [mm] | a0 [mm] | AREA RATIO | MEASUREMENT ERROR [±%] |
|---|---|---|---|---|---|
| EXAMPLE 1 | 0.4 | 10.0 | 3.38 | 5.9 | 3 |
| EXAMPLE 2 | 0.2 | 5.4 | 3.38 | 1.0 | 7 |
| EXAMPLE 3 | 0.4 | 6.0 | 3.38 | 1.5 | 6 |
| EXAMPLE 4 | 0.4 | 12.5 | 3.38 | 9.7 | 3 |
| EXAMPLE 5 | 0.4 | 15.0 | 5.00 | 6.1 | 5 |
| EXAMPLE 6 | 0.4 | 20.0 | 5.00 | 11.6 | 3 |
| EXAMPLE 7 | 0.4 | 15.0 | 7.00 | 2.6 | 5 |
| COMPARATIVE EXAMPLE 1 | 0.1 | 5.1 | 3.38 | 0.8 | 15 |
| COMPARATIVE EXAMPLE 2 | 0.2 | 7.7 | 5.00 | 0.9 | 13 |
| COMPARATIVE EXAMPLE 3 | 0.4 | 11.0 | 7.00 | 0.9 | 13 |

Figure 10:
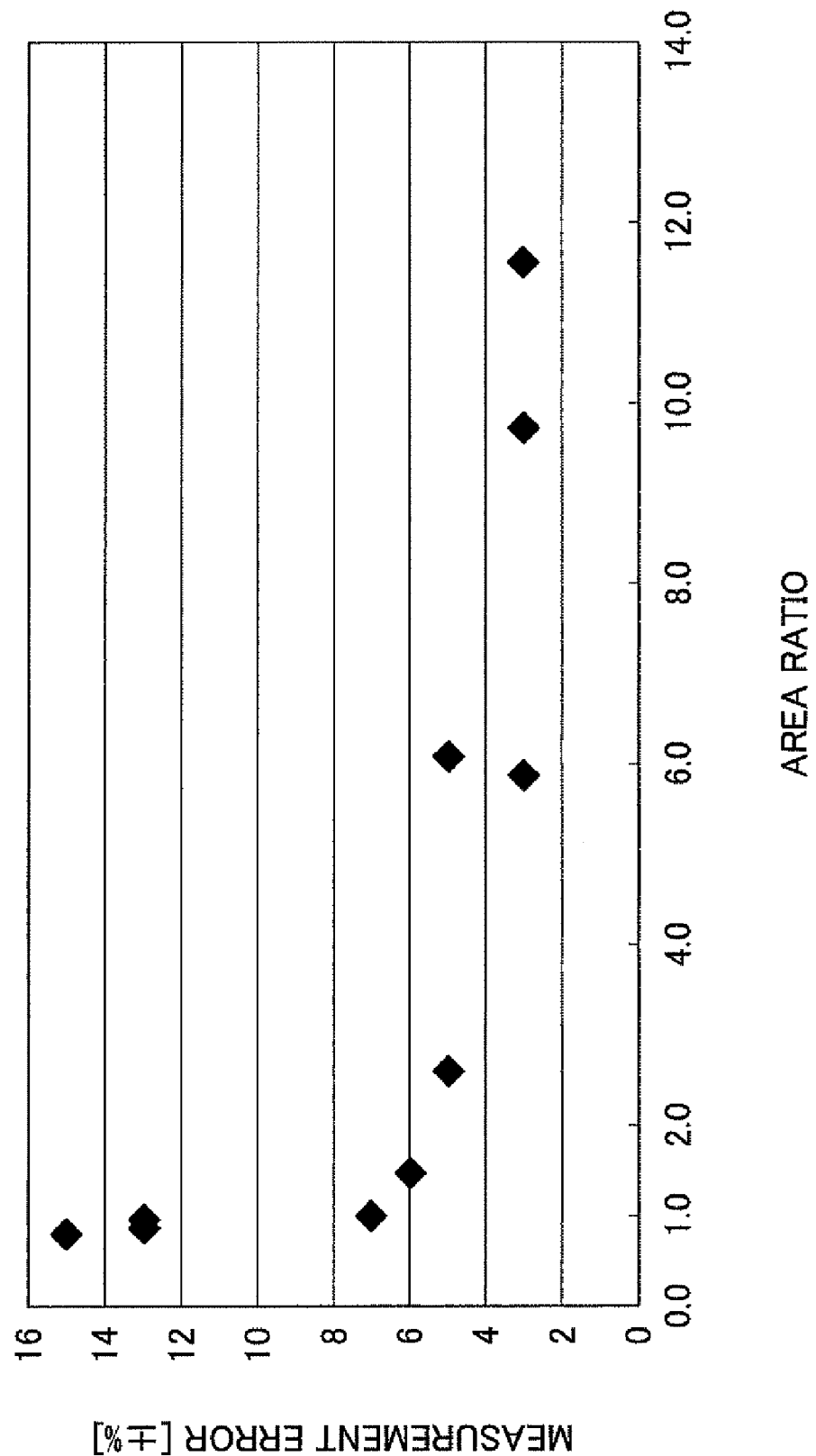
FIG. 10 is a graph showing relationships between area ratios and measurement errors of the particulate matter concentration measuring apparatus according to the first embodiment of the present invention.

FIG. 10 is a graph showing the relationships between the Area ratios and the Measurement errors in Table 1.

As shown in FIG. 10, the measurement error of the particulate matter concentration measuring apparatus 40PM varies mainly depending on the Area ratio and abruptly becomes worse more than 10% when the Area ratio is reduced to less than 1.0. The reason of the increase of the measurement error is considered that when the Area ratio is reduced to less than 1.0, the volume between the housing 42E and the cell 42b is reduced, which suggests that a factor other than soot deposited in the particulate matter detection filter 42A influences the measurement of the differential pressure.

Figure 12:
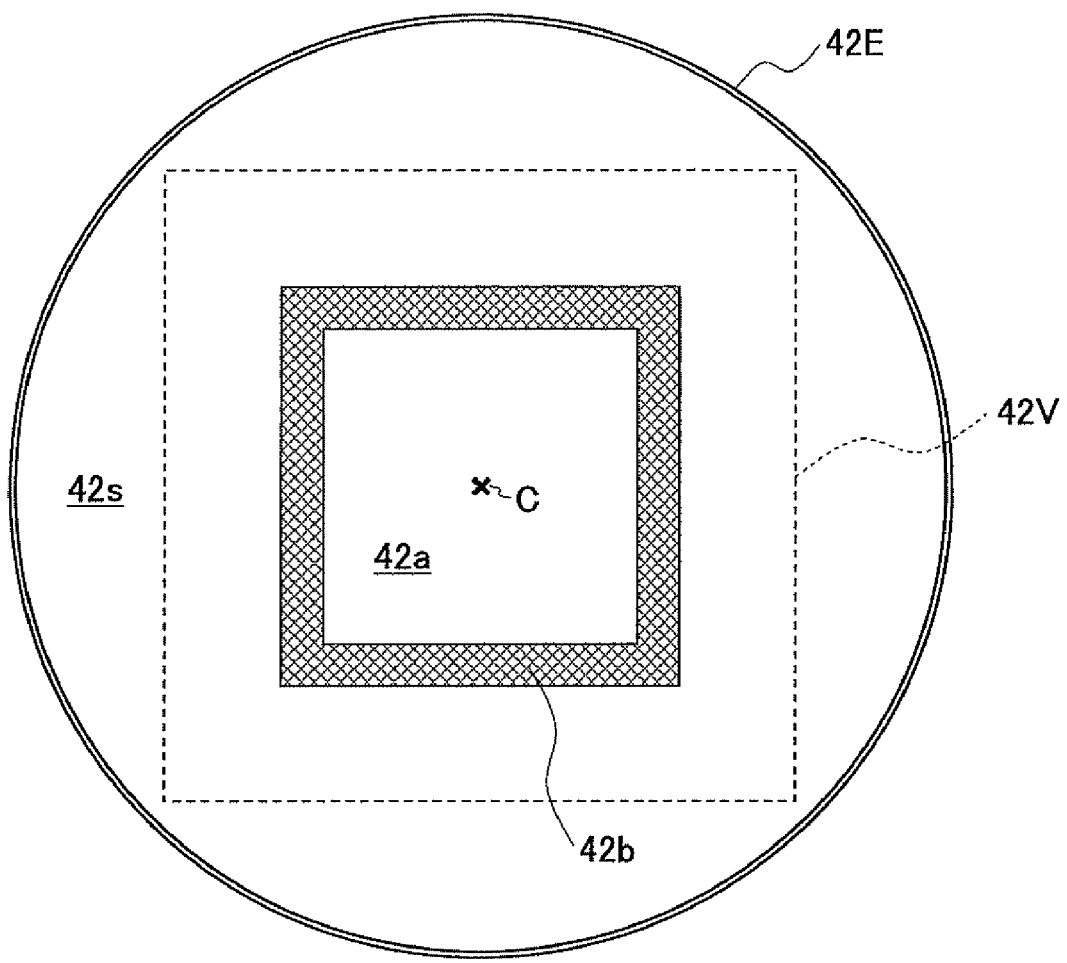
FIG. 12 is a drawing showing another modification of the first embodiment of the present invention.

Based on the result from the graph shown in FIG. 10, according to this embodiment of the present invention, it is proposed that, in the particulate matter concentration measuring apparatus 40PM shown in FIGS. 2 and 5, the Area ratio of the cross-section perpendicular to a central axis "c" (extending in the longitudinal direction of the cell 42b at the center of the cross section perpendicular to the longitudinal direction of the cell 42b as shown in, for example, FIG. 12) be equal to or more than approximately 1.0, preferably equal to or more than approximately 1.5.

Especially, according to this embodiment of the present invention, the central axis "c" of the cell 42b is substantially equal to the central axis of the housing 42E. In such configuration, by setting the Area ratio to a value equal to or more than approximately 1.0, preferably equal to or more than approximately 1.5, it may becomes possible to effectively reduce the influence of a factor other than soot deposited in the particulate matter detection filter 42A on the value detected by the differential pressure sensor 42B.

According to this embodiment of the present invention, as the particulate matter detection filter 42A, the cell 42b including the exhaust gas collection section 41a in the center portion on one end of the cell 42b is formed so that the shape of the cross-sectional areas of the cell 42b and the opening of the exhaust gas collection section 41a is a rectangular shape, the cross-sectional area being perpendicular to the central axis "c". Further, the cross-sectional shape along the inner surface of the housing 42E is substantially circular shape. However, for example, the cross-sectional shape along the outer surface of the housing 42E may be any shape so as to match the design of a vehicle in which the particulate matter concentration measuring apparatus 40PM is used.

Figure 11:
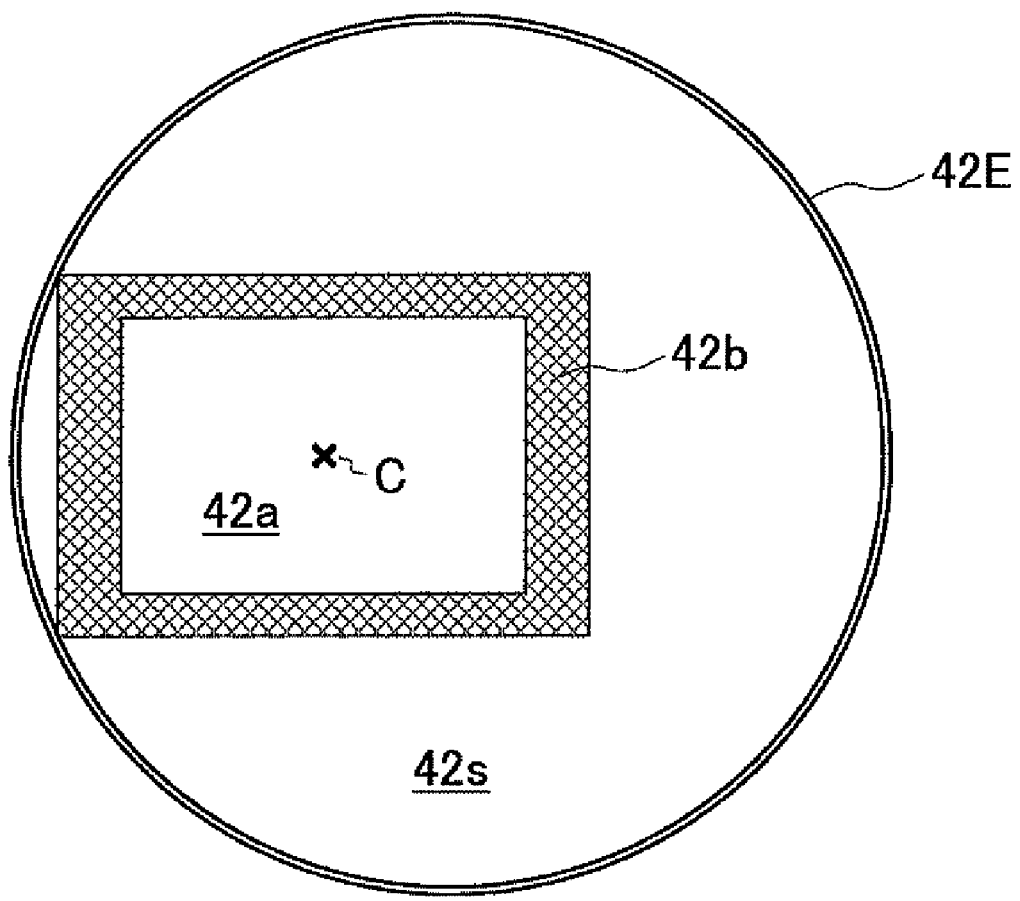
FIG. 11 is a drawing showing a modification of the first embodiment of the present invention.

However, as shown in an extreme example according to the first embodiment of the present invention as shown in FIG. 11, even in a case where the central axis "c" of the cell 42b having a rectangular cross-sectional shape is shifted from the position where the central axis of the housing 42E is disposed so that apart of the cell 42b becomes in contact with the inner surface of the housing 42E, when the Area ratio is equal to or more than approximately 1.0, preferably equal to or more than approximately 1.5, it may become possible to provide sufficiently accurate particulate matter concentration measurement. Therefore, embodiments of the present invention also include such configuration as shown in FIG. 11. In FIG. 12, the dotted line 42V defines a virtual space having the same central axis as the central axis "c" of the cell 42b and the shape similar to that of the cell 42b.

Figure 13:
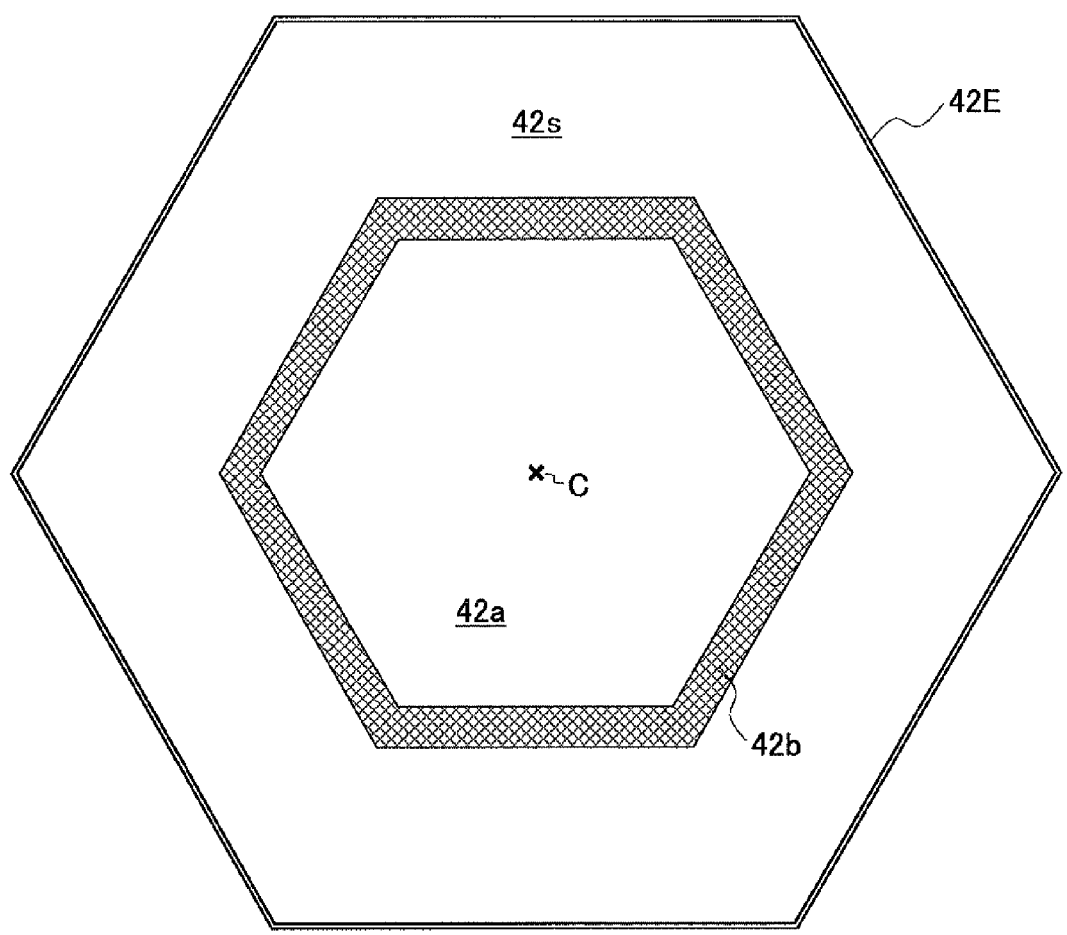
FIG. 13 is a drawing showing still another modification of the first embodiment of the present invention.

Further, in this embodiment of the present invention, the cross-sectional shape of the cell 42b may be any substantially polygonal shape such as a substantially pentagon and substantially hexagon. In such a case, in order to ensure enough outer space 42s, as shown in FIG. 13, the cross-sectional shape of the housing 42E may be the substantially similar shape corresponding to the cross-sectional shape of the cell 42b. Preferably, the cross-sectional shape of the cell 42b and the housing 42E is substantially circular shape to provide smoother flow of exhaust gas. In FIGS. 12 and 13, the same reference numerals are used for the same or equivalent elements described above and the descriptions thereof may be omitted.

Next, an upper limit of the Area ratio is considered below. From the viewpoint of the flow of exhaust gas passed through the cell 42b, no theoretical upper limit is placed. However, there may be some cases where a heater 42h is provided on the outer surface of the cell 42b to regenerate the cell 42b as described in the following embodiment of the present invention. In this case, when the Area ratio is too large, even if the heater 42h is driven to regenerate the cell 42b, the heat from the heater 42h may be irradiated to the outer space 42s; and as a result, the desired increase in temperature of the cell 42b may not be achieved. From this point of view, preferably, the Area ratio does not exceed approximately 10.0.

Figure 14:
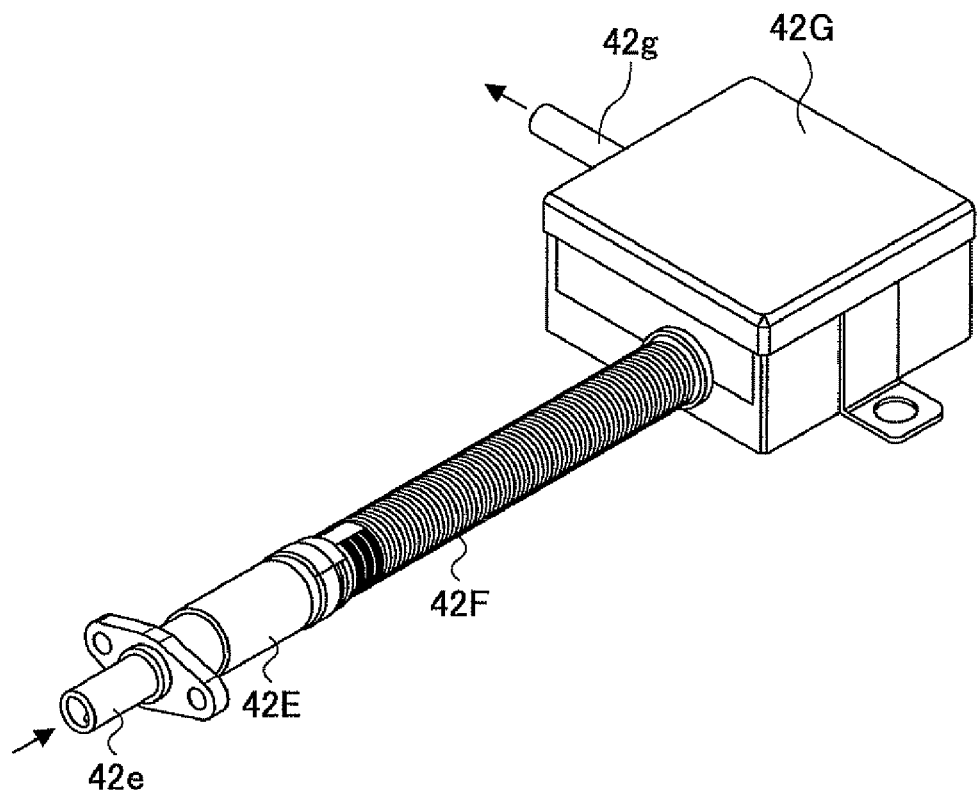
FIG. 14 is a drawing schematically showing the entire configuration of the particulate matter concentration measuring apparatus according to the first embodiment of the present invention.

FIG. 14 shows an exemplary appearance of a particulate matter concentration measuring apparatus 40PM according to this embodiment of the present invention. As shown in FIG. 14, the particulate matter concentration measuring apparatus 40PM includes the housing 42E having a pipe (tube) shape and made of heat-resistant metal such as stainless, and a header 42e provided on one end of the housing 42E so as to be inserted into and fixed to the exhaust line 21 shown in FIG. 2 on the downstream side of the Diesel Particulate Filter (DPF) 22. In the housing 42E, there is provided the particulate matter detection filter 42A made of porous ceramic material such as, preferably, Silicon Carbide (SiC). In this case, the header 42e constitutes the exhaust gas collecting line 41A to be inserted into the exhaust line 21.

Further, according to the first embodiment of the present invention as shown in FIG. 14, from the other end of the housing 42E, a flexible hose 42 is extended to the downstream end where there is provided a flow rate control unit 42G storing (housing) the differential pressure sensor 42B and the flow meter 44. Exhaust gas passed through the control unit 42G is exhausted into an exhaust tube 42g.

Having such a configuration described above, the desired particulate matter concentration measuring apparatus may become smaller; therefore, it may become easier to install the particulate matter concentration measuring apparatus at a desired place in a vehicle on an as-needed basis.

Figure 15:
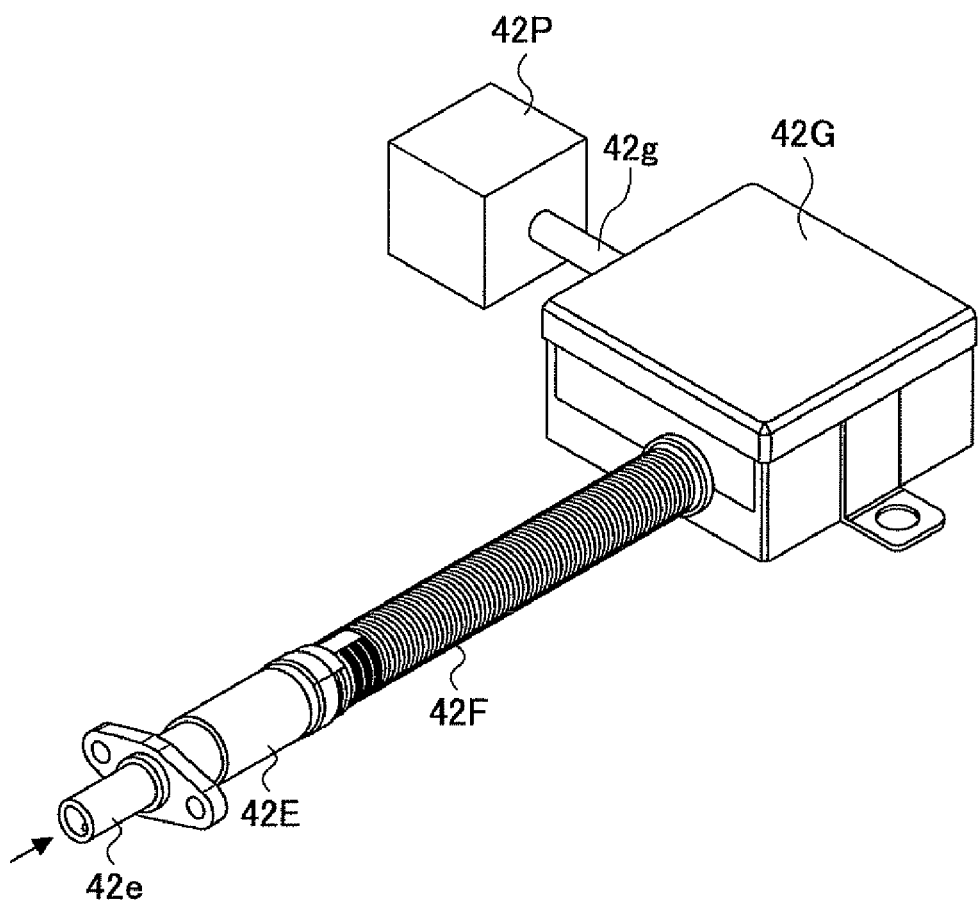
FIG. 15 is a drawing schematically showing a modification of the particulate matter concentration measuring apparatus according to the first embodiment of the present invention.

In the first embodiment of the present invention, as shown in FIG. 15, according to configuration of FIG. 14, a pump 42P may be connected to the exhaust tube 42g for exhausting exhaust gas from the flow rate control unit 42G so that the exhaust gas can be forcibly exhausted. By having the pump 42P, due to the negative pressure generated by the pump 42P, exhaust gas can be suctioned into the particulate matter concentration measuring apparatus and the desired particulate matter concentration measurement can be performed even in an atmosphere where there is no flow of exhaust gas through the header 42e.

Second Embodiment

Figure 16:
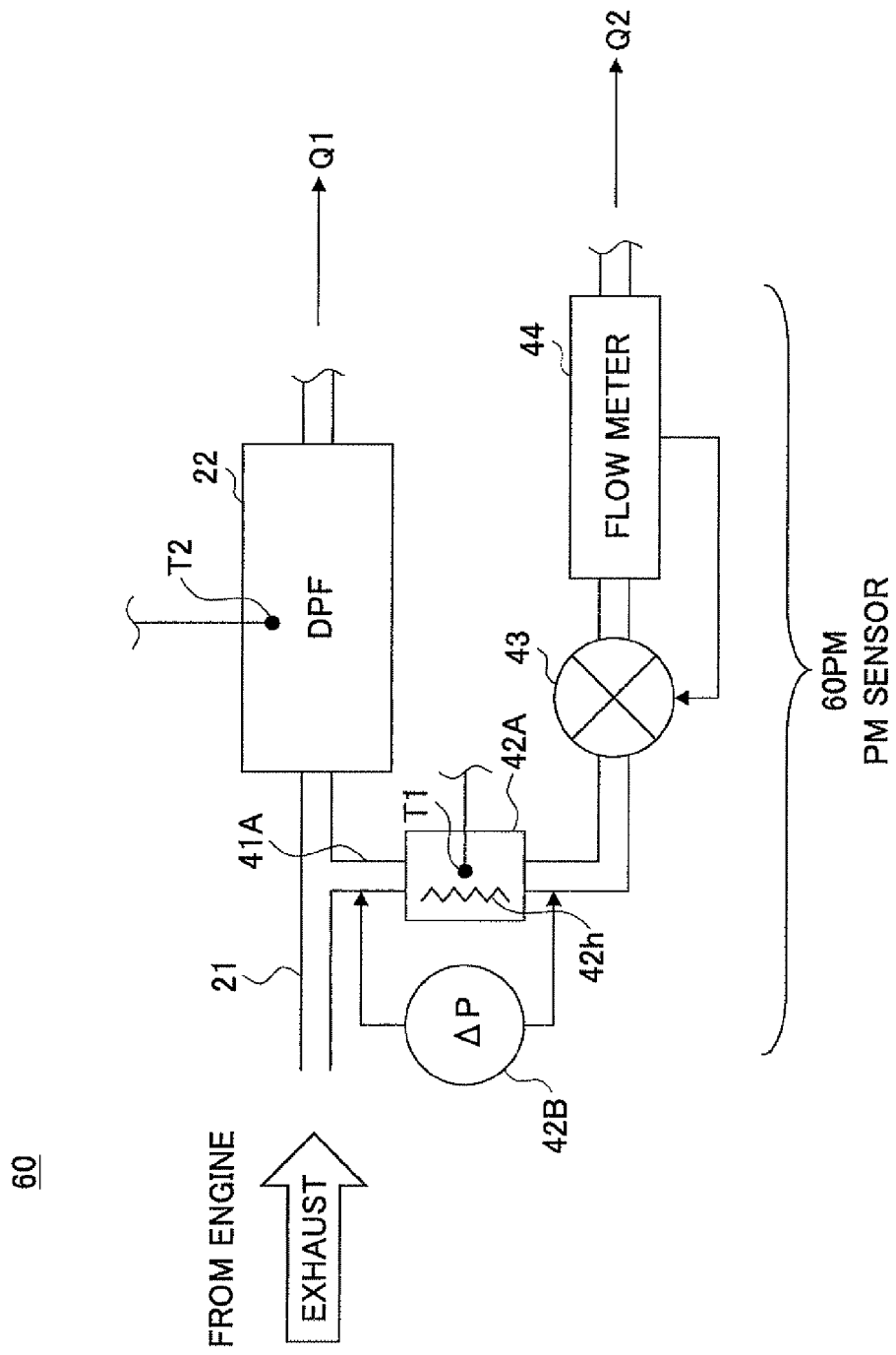
FIG. 16 is a drawing schematically showing an exemplary configuration of an exhaust gas purification apparatus using a particulate matter concentration measuring apparatus according to a second embodiment of the present invention.

FIG. 16 shows another exemplary configuration of an exhaust gas purification apparatus 60 for purifying exhaust gas from a diesel engine, the exhaust gas purification apparatus 60 including a particulate matter concentration measuring apparatus 60PM (PM sensor).

According to a second embodiment of the present invention shown in FIG. 16, the exhaust gas purification apparatus 60 has a similar configuration to that of the exhaust gas purification apparatus 20 in FIG. 1 in that there is the exhaust gas collecting line 41A having the exhaust gas collection section 41a connected to the exhaust line 21 on the upstream side of the Diesel Particulate Filter (DPF) 22.

In the configuration according to the second embodiment of the present invention as shown in FIG. 16, exhaust gas not having been passed through the Diesel Particulate Filter (DPF) 22 is collected by the particulate matter detection filter 42A, and based on the amount of particulate matter (PM) collected by the particulate matter detection filter 42A, in addition to the calculations according to formulas (1) through (3), the process described below is performed.

The value of "PMconc [g/m$^3$]" (i.e., the concentration of the particulate matter (PM) in exhaust gas in the exhaust gas collecting line 41A) is the same as that in the exhaust line 21, and therefore, a value of "PMenter-full-filter [g/h]" which is an amount of particulate matter (PM) passing through the exhaust line 21 is obtained according to the following formula (4):

$$PM\text{enter-full-filter [g/h]}=PM\text{conc [g/m}^3\text{]}\times Q1\text{ [m}^3\text{/h]} \quad \text{formula (4)}$$

where, the symbol "Q1" denotes the flow amount of exhaust gas in the exhaust line 21.

By doing this, it may become possible to estimate the amount of particulate matter (PM) accumulated in the Diesel Particulate Filter (DPF) 22. Herein, the symbol "Q1" denotes the flow amount of exhaust gas passing through the Diesel Particulate Filter (DPF) 22. The value of "Q1" may be directly measured or may be estimated based on the engine operation state.

In the configuration according to the second embodiment of the present invention shown in FIG. 16, there is provided a valve 43 in the exhaust gas collecting line 41A, and same as the case of the valve 23 of the conventional particulate matter concentration measuring apparatus 20PM of FIG. 1, the valve 43 may be controlled by the flow meter 44 so that the flow amount of exhaust gas in the exhaust gas collecting line 41A is maintained at a predetermined value "Q2".

Further, in this configuration, as time elapses, particulate matter (PM) is gradually deposited on the particulate matter detection filter 42A (cell 42b); therefore, the particulate matter detection filter 42A is to be regenerated.

To regenerate the particulate matter detection filter 42A, there is provided the heater 42h on the particulate matter detection filter 42A (cell 42b). By driving the heater 42h on an as-needed basis by using power from a driving line, the heat from the heater 42h burns and removes the particulate matter (PM) including Carbon (C) as a main component and collected on the cell 42b so as to regenerate the particulate matter detection filter 42A.

According to this embodiment of the present invention, it may be possible to obtain the same effect as that in the first embodiment of the present invention.

The present invention is described above by referring to preferable embodiments. However, the present invention is not limited to the specific embodiments, and within the scope of the appended claims, various modifications, transformations, alteration, exchanges, and the like may be made without departing from the scope and spirit of the present invention. For example, in the above embodiment, the flow rate meter 44 may be removed, provided that the flow rate of exhaust gas passing through the exhaust gas collecting line 41A is known. Further, the temperature sensor T1 may also be removed, provided that characteristic of exhaust gas is assumed to be constant. Further, the heater 42h may also be removed provided that the regeneration process is not necessary. Further, the valve 43 may also be removed when the flow rate is being accurately measured. Further, the heater 42h used in the second embodiment of the present invention may also be used in the particulate matter concentration measuring apparatus in the first embodiment of the present invention.

According to an aspect of the present invention, exhaust gas having passed through the particulate matter detection filter may flow to the downstream side without being left or held and as a result, it may become possible to accurately measure the differential pressure and accordingly, the concentration of particulate matter (PM) may be more accurately measured.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A particulate matter concentration measuring apparatus configured to measure concentration of particulate matter in exhaust gas passing through an exhaust line of a diesel engine, the apparatus comprising:
    an exhaust gas collecting line branched from the exhaust line and having a cross-sectional area smaller than a cross-sectional area of the exhaust line;
    a particulate matter detection filter provided in the exhaust gas collecting line;
    a differential pressure sensor configured to sense differential pressure between an inlet and an outlet of the particulate matter detection filter;
    a passage wall disposed so that the exhaust gas flows to a downstream side of the particulate matter detection filter;
    an inlet side passage through which the exhaust gas flows into the particulate matter detection filter in the passage wall; and
    an outlet side passage through which the exhaust gas flows out from the particulate matter detection filter, wherein
    the outlet side passage defines a space having an outlet side cross-sectional area approximately 1.0 times or more larger than an inlet side cross-sectional area of a space defined by the inlet side passage, the outlet side cross-sectional area and the inlet side cross-sectional area being substantially perpendicular to a longitudinal axis of the particulate matter detection filter.

2. The particulate matter concentration measuring apparatus according to claim 1, wherein
    the outlet side passage defines the space having the outlet side cross-sectional area approximately 1.5 times or more larger than the inlet side cross-sectional area of the space defined by the inlet side passage, the outlet side cross-sectional area and the inlet side cross-sectional area being perpendicular to the longitudinal axis of the particulate matter detection filter.

3. The particulate matter concentration measuring apparatus according to claim 1, wherein
    in a cross-sectional area perpendicular to the longitudinal axis of the particulate matter detection filter, the passage wall is disposed on or outside a virtual space having a same axis as the longitudinal axis of the particulate matter detection filter and a shape similar to a shape of the particulate matter detection filter and
    the virtual space has an area approximately 1.0 times or more larger than an area defined by an outer shape of the particulate matter detection filter.

4. The particulate matter concentration measuring apparatus according to claim 1, wherein
    a space defined by the passage wall is concentrically provided with the particulate matter detection filter.

5. The particulate matter concentration measuring apparatus according to claim 1, wherein
    the particulate matter detection filter has a cylindrical shape or a substantially tubular shape having a substantially polygonal cross section, each shape extending along the longitudinal axis, and the passage wall defines a space having a substantially cylindrical shape or a tubular shape having a substantially polygonal cross section, each shape extending along the longitudinal axis.

6. The particulate matter concentration measuring apparatus according to claim 1, wherein
the exhaust line is connected to a Diesel Particulate Filter having a filter capacity larger than a filter capacity of the particulate matter detection filter.

7. The particulate matter concentration measuring apparatus according claim 6, wherein
the exhaust gas collecting line is connected to the exhaust line at a downstream side of the Diesel Particulate Filter.

8. The particulate matter concentration measuring apparatus according claim 6, wherein
the exhaust gas collecting line is connected to the exhaust line at an upstream side of the Diesel Particulate Filter.

* * * * *